(12) United States Patent
Popescu

(10) Patent No.: US 10,952,696 B2
(45) Date of Patent: Mar. 23, 2021

(54) SENSOR ARRAY IN A COMPONENT OF AN IMAGING DEVICE

(71) Applicant: Siemens Healthcare GmbH, Erlangen (DE)

(72) Inventor: Stefan Popescu, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 279 days.

(21) Appl. No.: 15/998,718

(22) Filed: Aug. 16, 2018

(65) Prior Publication Data
US 2019/0053777 A1 Feb. 21, 2019

(30) Foreign Application Priority Data

Aug. 16, 2017 (EP) ..................... 17186492
Sep. 19, 2017 (EP) ..................... 17191898

(51) Int. Cl.
| A61B 6/00 | (2006.01) |
| A61B 5/055 | (2006.01) |
| G01R 33/38 | (2006.01) |
| G01R 33/385 | (2006.01) |
| G01R 33/3815 | (2006.01) |
| A61B 6/03 | (2006.01) |
| G16H 30/40 | (2018.01) |
| G16H 40/63 | (2018.01) |
| G01R 33/36 | (2006.01) |
| G01R 33/28 | (2006.01) |

(52) U.S. Cl.
CPC ............ *A61B 6/56* (2013.01); *A61B 5/055* (2013.01); *A61B 6/032* (2013.01); *A61B 6/581* (2013.01); *A61B 6/586* (2013.01); *G01R 33/3804* (2013.01); *G01R 33/385* (2013.01); *G01R 33/3815* (2013.01); *G16H 30/40* (2018.01); *G16H 40/63* (2018.01); *A61B 2560/0266* (2013.01); *G01R 33/28* (2013.01); *G01R 33/3692* (2013.01)

(58) Field of Classification Search
None
See application file for complete search history.

(56) References Cited

U.S. PATENT DOCUMENTS

| 2005/0109829 A1 | 5/2005 | Postma |
| 2006/0064491 A1 | 3/2006 | Ebert et al. |
| 2009/0243841 A1* | 10/2009 | Alsafadi .................. A61B 6/56 340/539.22 |

(Continued)

FOREIGN PATENT DOCUMENTS

WO WO-2007/143402 A2 12/2007

OTHER PUBLICATIONS

Popescu,: "Energy autonomous wireless sensors"; MR Tech briefs archive; pp. 1-4; ( 2017).

*Primary Examiner* — Douglas X Rodriguez
(74) *Attorney, Agent, or Firm* — Schiff Hardin LLP

(57) ABSTRACT

A method for detecting measurement signals during a medical imaging procedure executed by a medical device includes detecting measurement signals with a set of sensor nodes, which are integrated in a component of the medical imaging device, wherein each sensor node (SN) operates autonomously and wirelessly, and locally preparing the detected signals for being transmitted according to an interference-free instruction protocol, to a gateway.

17 Claims, 5 Drawing Sheets

(56) References Cited

U.S. PATENT DOCUMENTS

2012/0112747 A1* 5/2012 Alexiuk .............. G01R 33/288
  324/318
2015/0220763 A1* 8/2015 Porzelt .................. G08C 17/00
  340/10.1
2017/0281083 A1   10/2017 Sawano

* cited by examiner

SENSOR ARRAY IN A COMPONENT OF AN IMAGING DEVICE

BACKGROUND OF THE INVENTION

Field of the Invention

The present invention concerns methods, apparatuses and systems for sensor signal measurement for failure detection in complex imaging scanners, such as magnetic resonance scanners or computed tomographic apparatuses.

Description of the Prior Art

Medical imaging scanners are highly complex systems commonly including equipment parts or components that are subject to high stress factors, such as temperature extremes, pressure and mechanical vibrations, and accelerations during normal operation. For example, the gradient coil within an MR scanner are subject to high temperature gradients and strong mechanical vibrations at the same time. The X-ray detector and the X-ray generator mounted on the rotating CT gantry are subject to large mechanical accelerations and centrifugal forces as well as to large temperatures due to heating in normal operation. Yet, all these components are supposed to maintain extraordinary reliable operation for a maximum availability of the scanners in the clinical operation theatre as the patient lives and the most accurate diagnostics are vital goals in delivery of healthcare. With these considerations, there is a need for continuous monitoring of the scanner's operating condition using various sensors that provide operational data used to early detection of anomalies and replacement of parts before catastrophic failures. The information gathered from all scanners in the installed control computer could be further used to improve the scanner design such to eliminate weak points.

In state of the art, medical scanners today already integrate various sensors, mostly connected by wired interfaces to main electronic boards that implement high-level communication links toward the main system controller. Dedicated software is used to periodically read and process sensors data and save the data into log files. Furthermore, the main electronic boards implement various adjustments or supervision functions, such as temperature monitoring to avoid overheating or other malfunctions. However, each new sensor added to the system increases the overall costs and the complexity, since each new sensor needs to be wired-in so as to be supplied with energy and provided with a signal transmission path. Generally, the costs of wiring the respective sensor for communication purposes and to supply energy to the sensor commonly exceeds the cost of sensor itself. Hardware upgrades for legacy and older systems, such as upgrading to a new or improved component, like a new MR gradient coil, does not always allow for additional sensors in the new component as the existing wired interface does not support additional connections. A further limitation of prior art systems is that they allow sensors to be deployed at locations where no direct wired connection is possible or allowed. This is the case, for examples, for sensors placed inside the cryogenic environment of a superconducting magnet or deep inside the inner layers of a gradient coil when the additionally required sensor wiring will negatively impact the basic functionality of the component by causing unwanted collateral effects. A further example is sensors placed inside the vacuum of an X-ray tube, or built-in into the rotating anode of the X-ray tube.

Hence, there is a need in the state of the art to provide wired connections (for energy supply and for data exchange) to and from the sensors.

Therefore, there is a need to provide more sensor signals of an imaging device by assuring high quality of the sensor signals and of the operation of the imaging device. Further, failure detection and failure avoidance of the medico-technical devices should be improved. Moreover, there is a need to not impair the signals of the medical imaging device by sensor signal transmission. Also, it should be possible to make operation of the imaging device cheaper and subject to better technical diagnosis.

SUMMARY OF THE INVENTION

The above object is achieved according to the present invention.

According to a first aspect of the present invention, a method for detecting measurement signals during a medical imaging procedure executed by an imaging apparatus, such as magnetic resonance imaging (MR) or computed tomography (CT), has the steps of detecting measurement signals by a set of sensor nodes, which are non-detachably and permanently integrated in a component of the imaging apparatus, wherein each sensor node operates autonomously and wirelessly, and locally preparing the detected signals for being transmitted according to a set of transmission rules.

The invention is designed to solve the wiring problem in state of the art sensor based failure detection systems. In such state of the art systems, the sensors that are used have to be connected to a control computer for energy supply and for data transmission. This was done based on wired connections. The invention solves this problem by providing autonomous sensors, which do not need external energy supply and which produce their own energy. Further, the sensors use a wireless connection for data transmission. In the wireless connection, a specific protocol, namely an interference-free instruction protocol is implemented for instructing the sensor nodes from the gateway. Moreover, a set of transmission rules is applied for the transmission of the detected measurement signals to the gateway. The protocol and the set of rules are for assuring, that sensor transmission has no interference with detection and/or transmission of imaging signals, provided by the MR or CT apparatus.

With this solution, security of the imaging apparatuses can be improved by detecting possible errors and failures as early as possible. Further, maintenance of the technical systems may be simplified to a large extent. Due to the fact that now sensors may be located at positions within the imaging device where it was not possible in prior art systems (e.g. because a wired connection was not possible at that location), an extended signal detection and analysis may be executed.

Security is further improved by the use of a special protocol, a so called interference-free instruction protocol is used for data transmission of the sensor node data to the gateway. The interference-free instruction protocol correlates transmission of the sensor node signals to the operating mode of the medical device. In a preferred embodiment, the medical apparatus is a MR scanner. In this case, the interference-free instruction protocol defines that the sensor node system is operated in an UNMUTE mode when the MR scanner is not in a READOUT sequence (i.e. during RFE or during GRAD-ENC phase, which will be explained in more detail in the detailed description) and in a MUTE mode if the MR scanner is operated in a READOUT phase, in which no data transmission will be executed. In the UNMUTE mode the sensor node harvests energy from the RF energy of the MR apparatus, if the MR device is in a RFE sequence and harvests vibrational energy of the MR apparatus, if the MR device is in a GRAD-ENC sequence.

The UNMUTE instruction serves to initiate an UNMUTE mode, which is activated during a RFE and GRAD-ENC phase of an MR imaging apparatus.

The MUTE instruction serves to initiate a MUTE mode, which is activated during a READOUT of an MR imaging apparatus.

In the following a short definition of terms is given.

The imaging apparatus is a medical technical apparatus for acquiring medical images. It is preferably an MR apparatus and the component built into the scanner may be a gradient coil or a magnet, in particular, a cryogenically cooled magnet. In another embodiment, the imaging apparatus is a CT apparatus and the component is an X-ray tube or high voltage generator, which may be mounted on the rotating gantry of the CT scanner.

The component is a built-in structural element of the imaging apparatus. As explained above, it may be a gradient coil or a magnet or another basic element in the imaging apparatus. The component is essential for functioning of the imaging device and its functionality needs to be maintained and assured for providing required quality of the medical imaging system. For this reason, sensor data, which are detected during operation of the imaging apparatus at the respective component serve as key input data for the assessment of an operational state (the operational state may for example indicate an error-prone state, wherein errors are probable, a state without probability of upcoming failures and a failure-state).

The sensors are adapted to detect (measure) analog signals (which may be converted in digital data) during operation of the component within the medical imaging device. The sensors are located and integrated in a sensor node. The sensors are adapted to detect a temperature value, vibration amplitudes and/or mechanical stress (e.g. strain gauge) and other signals, which are relevant for operating the respective components, such as voltage, acceleration, pressure, and/or humidity values and/or values relating to an electrostatic field or magnetic field (field strength values) or flow speed of a cooling agent like air or water. The sensors detect the signals locally. The sensors transmit the detected signals to their sensor node, in which they are built-in. The sensors are integrally formed in a non-detachable manner (permanently built-in or casted-in) on the sensor node as one piece. The sensor(s) are not separable from the sensor node and thus are inextricably combined with the node.

The sensor node is an electronic device, which may be implemented as a chip assembly, namely on a printed circuit board (PCB). The sensor node includes the sensor as such, or a number of sensors and a storage (memory) and an interface for signal transmission and reception of instructions for operating the sensor node (communication unit). The sensor node may additionally have a processor, which may serve to execute the received instructions from a gateway and which may serve for pre-processing of detected measurement signals. The interface may be implemented as a wireless interface, preferably as a radio frequency communication interface. The sensor node, thus, is operated fully wirelessly and does not necessitate wired connections. Further, the sensor node is operated autonomously, which means that it does not need to be provided with external electricity. In a preferred embodiment, the sensor node even still does not comprise a battery. This feature extends lifetime of the sensor node. It uses energy harvesting methods and generates its electricity by its own. In a first embodiment, photovoltaic is used for producing electricity. In a second embodiment, vibrations of the component are used for electricity production and a third and fourth embodiment refer to using environmental thermo-electrics and RF-radiation for producing electricity. Each sensor node has its own power station for energy (electricity) production. There is no need to provide them with external electricity. Each sensor node is integrally formed in a non-detachable manner (permanently built-in or even casted-in) in the component as one piece. The sensor node is cast in the component during fabrication of the latter and is not separable without disassembling the imaging device or the component.

The gateway is an electronic circuit and is preferably located in the control computer of the imaging device. The gateway is in wired connection to further processing systems (e.g. for failure detection).

The interference-free instruction protocol is a set of rules for the transmission of the detected measurement signals and/or data to and from the sensors. The interference-free instruction protocol is a protocol which allows optimal data transmission ("optimal" referring to bandwidth and signal power) by assuring a high quality operating mode of the medical device. The protocol includes rules for data transmission so that the signals and operation of the medical device will not be impaired. In a preferred embodiment, the interference-free instruction protocol is a set of instructions, produced and issued by the gateway for reception and processing on the sensor nodes. In another preferred embodiment, the medical device is an MR scanner and then, the interference-free instruction protocol specifies the transmission of the sensor signals in order to avoid interference from the radio frequency signals, used to transmit the detected measurement signals of the sensors and the signals of the imaging device. This aspect ensures and safeguards that there is no disturbance of and no interfering with the medical signals.

A further important aspect of the invention concerns an approach to avoid losing data due to full energy exhausting at a sensor node. This aspect is particularly relevant for a MR scanner and for sensors nodes harvesting energy out of scanner vibrations generated by pulsation of the gradient coils. The gradient coils in the MR scanner are active only during imaging, which is when the scanner acquires data using MR sequences that generate pulsed gradient currents. Out of this measurement time, the scanner is quiet and the level of vibrations is considerable lower. However, it is necessary to be further log the information provided by the wireless sensor nodes, such as temperature monitoring nodes are required e.g. for the inline monitoring of cooling reserve. In this case there is a risk that the harvested energy available at a sensor node exhausts after a while and the sensor would then be unable to perform the intended function.

Therefore, according to a preferred embodiment, the method includes an automatic data-loss-prevention procedure (routine), which initiates energy-provision functions for further operating the sensor node in case of low energy.

The data-loss-prevention procedure includes sending an SOS message by the sensor node to the gateway, if a local energy reserve on the sensor node is detected to decrease under a pre-definable first threshold.

In a preferred embodiment, an automatic mode change is triggered on the sensor node, in case it is detected that the local energy reserve on the sensor node decreases under the pre-definable first threshold. In particular, the sensor node is automatically transferred in a MUTE mode (which is explained in more detail below). If it is detected that the local energy reserve on the sensor node decreases under a pre-definable second threshold, in a further preferred embodiment, the sensor node is automatically transferred in a SLEEP mode (which is also explained in more detail below).

The energy-provision function is initiated by the gateway in reply to receiving the SOS message from the sensor node, so that the gateway sends an instruction to the imaging device for activating the component, for example by activating the gradient coil or by moving the CT gantry, for the purpose of providing energy (vibrational energy).

Thus, in order to avoid the risk of data loss, the following functions are added to the system:

SOS message/imminent energy exhaustion.
  When the local energy stored at sensor nodes decreases below a pre-defined first threshold level, which means that there is an imminent risk for that sensor node to fully exhaust its local energy, it sends an SOS message to the gateway. The gateway in turn initiates a process that allows the nodes to reload the local energy storage. For the MRI example mentioned above the gateway sends a request to the scanner control system to activate the gradients and thereby to generate mechanical vibrations that the sensor nodes reuse to harvest energy.

HIBERNATION mode (automatic MUTE followed by SLEEP mode)
  When approaching the risk of fully exhausting the local stored energy the sensor node sends an SOS message and automatically enters the MUTE mode in order to save energy by disabling the data transmission to the gateway. The sensing and storage of newly acquired data continues again as long as the available energy still allows for it. If the energy reserve further decreases below a second pre-defined threshold, the sensing activity is also disabled and the node enters the SLEEP mode to preserve the local data as long as possible.

RELAY emergency retransmission mode
  When the local available energy is low the transmit power and the transmission range of the sensor node may decrease. In this situation and if a node is spatially local at a distance from the gateway it may be possible that some message sent by this node is not received correctly and thus not acknowledged by the gateway. In many standard communication protocols, it is common practice that the gateway broadcasts an acknowledge message ACK to confirm correct reception of a message originated from a network node, i.e. from a sensor node. For high priority messages like an SOS message this would lead to further malfunctions in the network. To avoid this situation the closest local sensor node that correctly received the SOS message and gets the first free transmission slot implements a RELAY mode by retransmitting the SOS message with the originator SENDER-ID toward the gateway. Thus, if at least one sensor node has issued an SOS message, this will be broadcasted to all other sensor nodes before being transmitted to the gateway. The first sensor node, which gets the option for transmission according to the protocol, then implements the RELAY emergency transmission mode for sending the received SOS message together with an originator address (identification of the out of energy sensor node) to the gateway.

It should be noted, that the three functions/modes, as mentioned above, are not limited to the exemplary embodiment of the MR scanner. Thus, these aspects and features can also be used with a CT scanner, whereby the sensor nodes harvest vibrational energy out of the gantry rotation. During pause time in-between patient scans the scanner control stops the gantry rotation but it will be restarted by an SOS message.

In another preferred embodiment, the interference-free instruction protocol implements or helps to execute the set of (pre-definable) rules for transmission of the detected measurement data to the gateway. The rules are MR-sequence aware, i.e. they depend on the actual MR-sequence or time phase during image acquisition. During sensible time phases, for example during READOUT, signal transmission of the sensor nodes to the gateway has to be suspended for not impairing the medical signals. One rule, therefore, is, to interrupt or suspend signal transmission during READOUT. This may be controlled by the gateway by issuing a MUTE instruction or even a SLEEP instruction in case a READOUT is detected. In case the READOUT phase has ended and this has been detected automatically by the gateway or this information has been provided by other modules to the gateway, the gateway may in turn issue an UNMUTE instruction in order to resume data transmission or a WAKEUP instruction in order to resume data logging of the sensor nodes again.

Detected measurement data (converted signals or data) will only be transmitted from the sensor nodes to the gateway in case a WAKEUP or UNMUTE instruction has been received before. Thus, transmission according to the rules is ensured.

In a preferred embodiment, the instructions are sensor node specific so that each of the respective sensor nodes may be addressed in a dedicated manner. This has the advantage, that each of the sensor nodes may be addressed separately. Thus, it is possible, to instruct a first set of sensor nodes differently as a second set, which for example may be located at a different position in the imaging device or which may serve to detect other signals.

In a preferred embodiment, the interference-free instruction protocol comprises the following instructions for instructing the sensor nodes by the gateway:
  a SLEEP instruction, which serves to execute a SLEEP function on the sensor node. In order to avoid interference with the MR signals, the gateway issues this SLEEP instruction, which reduces local activity on the sensor node to a minimum. Particularly, the SLEEP instruction will be issued during a READOUT phase of a MR sequence as this phase during MR acquisition is most vulnerable for disturbance and interference.
  a WAKEUP instruction, which serves to execute a WAKEUP function on the sensor node. This is the corresponding function after the sensor node has been set to SLEEP. The WAKEUP function serves to activate the sensor node again. In the WAKEUP state, the locally (on the sensor node) detected signals may be processed (e.g. converted with A/D converter) and sent to the gateway.
  a MUTE and a respective UNMUTE instruction, which serve to execute a MUTE and UNMUTE function on the sensor node, in order to avoid interference with the MR signals. In the MUTE state, signals may still be detected, but data transmission to the gateway is inhibited. After READOUT period of the MR scanning procedure, the UNMUTE instruction may be sent again, which again allows signal transmission.
  a TIME SYNC instruction, which is that which serves to adjust the local clock on the sensor node with the gateway clock, so that sensor node signals may be transmitted time-resolved, in particular with a timestamp.

Generally, the instructions of the gateway are issued by and sent from the gateway. The instructions may be broadcasted to all or to selected sensor nodes for local execution on the sensor node.

The instructions may be sensor node specific, so that a particular sensor node or a group of sensor nodes may be addressed dedicatedly. For example, a first sensor node at a first location may be instructed with other instructions as a second sensor node at a second location. The instructions may, thus, be location-aware (dependent of the location of the respective sensor node) and may also be aware of other aspects, i.e. depending on the function (e.g. type of measurement signals to be detected) or depending on the purpose of later data processing. In particular, the instruction may include an instruction element for pre-selecting required data locally on the sensor node for only transmitting a selection of data to the gateway. The pre-selection may be dependent on the type of data (for example some physical values change slower over time (e.g. temperature) as others (e.g. current). For example, for the slowly changing signals only an average value may be required to be transmitted to the gateway. Other instructions may refer to activating or deactivating the configuration settings for transmission. Other instructions may refer to a setting of the sampling rate of the sensor nodes or to filter characteristics, which may be applied locally on the sensor nodes.

Locally preparing the detected measurement signals means to forward the data to an output interface of the sensor node for transmission to the gateway. This is, however, a very thin client solution of a sensor node. In a preferred embodiment, the sensor node may additionally include a processing unit for pre-processing the detected measurement signals for transmission. Pre-processing may comprise, storing or buffering the data before they are sent. Pre-processing may comprise a conversion in another format or a compression of the data for saving bandwidth of data transmission. Other types of pre-processing are mentioned above with respect to the instructions, such as pre-selecting sensor data or apply filter operations.

The sensor node interacts with the gateway via a wireless protocol, in particular, over a radio frequency communication channel. It may be a point-to-multipoint connection. The communication channel between the sensor node and the gateway preferably is bidirectional, which has the advantage that the sensor node may be controlled centrally by the gateway, in particular by the interference-free instruction protocol.

Another aspect of the invention concerns a component in an imaging apparatus, wherein a set of wireless and autonomous sensor nodes is integrated in and fabricated in one piece with the component during a component fabrication process, wherein each sensor node includes:
- an energy supply unit for providing electricity for operating the sensor node (e.g. piezoelectric transducer),
- at least a sensor for detecting at least one type of measurement signal,
- a communication unit (e.g. an antenna) and
- a storage for locally storing the detected measurement signals. In a preferred embodiment, the sensor node (except its antenna) is shielded with a (slotted) copper sheet enclosure for avoiding signal interference. This feature further improves quality and ensures that no interference with medical signals will exist.

Another aspect of the invention concerns a system in an imaging apparatus with a component, described above and with a gateway for controlling the measurement process.

Moreover, the invention concerns a method for operating a gateway and a method for fabricating a gradient coil according to the aspects described above.

The present invention also encompasses a non-transitory, computer-readable data storage medium encoded with programming instructions (program code) that, when the programming instructions are distributively loaded into components of a system as described above, cause the components to collective operate so as to implement any or all embodiments of the operation described above.

DESCRIPTION OF THE PREFERRED EMBODIMENTS

In the following description, for purposes of explanation and not limitation, specific details are set forth, such as particular network environments and communication standards etc., in order to provide a thorough understanding of the current invention. It will be apparent to one skilled in the art that the current invention may be practiced in other embodiments that depart from these specific details. For example, the skilled person will appreciate that the current invention may be practiced with any wireless network like for example a wireless sensor network (WSN) which may communicate via 6LoWPAN and 802.15.4e standards or an IP-based network. Further, different data communication protocols may be used in this network, depending on the application requirements, including data-centric protocols, like SPIN, Directed Diffusion, Rumor Routing, COUGAR, ACQUIRE, EAD, Information-Directed Routing, Gradient-Based Routing, and location-based protocols, including MECN, SMECN, GAF, GEAR. As another example, the invention may also be implemented with different types of gateways as a control node. The gateway may be integrated into the medical device or may be externally provided as a separate module in the examination room. The invention may also be used in a cloud computing network and/or according to other internet-of-things standards. For example, similar communication mechanisms may be used for a wider range of radio technologies, including ITU-T G.9959 (as used in Z-Wave, RFC 7428), and the Digital Enhanced Cordless Telecommunications (DECT) Ultra Low Energy (ULE) cordless phone standard.

The present invention proposes a robust mechanism for the detection and wireless transmission and processing of sensor data in a medical environment. In a broad sense, the invention refers also to controlling a set of sensor nodes in a specific manner, so that interference with medical sensor signals may be prevented.

The invention provides a procedure for secure transmission of locally detected sensor data to a central gateway for failure detection and analysis of operational conditions of the component in the medical device, wherein the component or the medical device transmits sensible medical data which have to be secured and protected against interference. The medical device is typically an imaging device.

A wireless sensor network (WSN) is a wireless network consisting of spatially distributed autonomous devices using sensors to monitor physical or operational conditions (of the technical system). A WSN system incorporates a gateway that provides wireless connectivity back to the wired system and distributed nodes.

Figure 1:
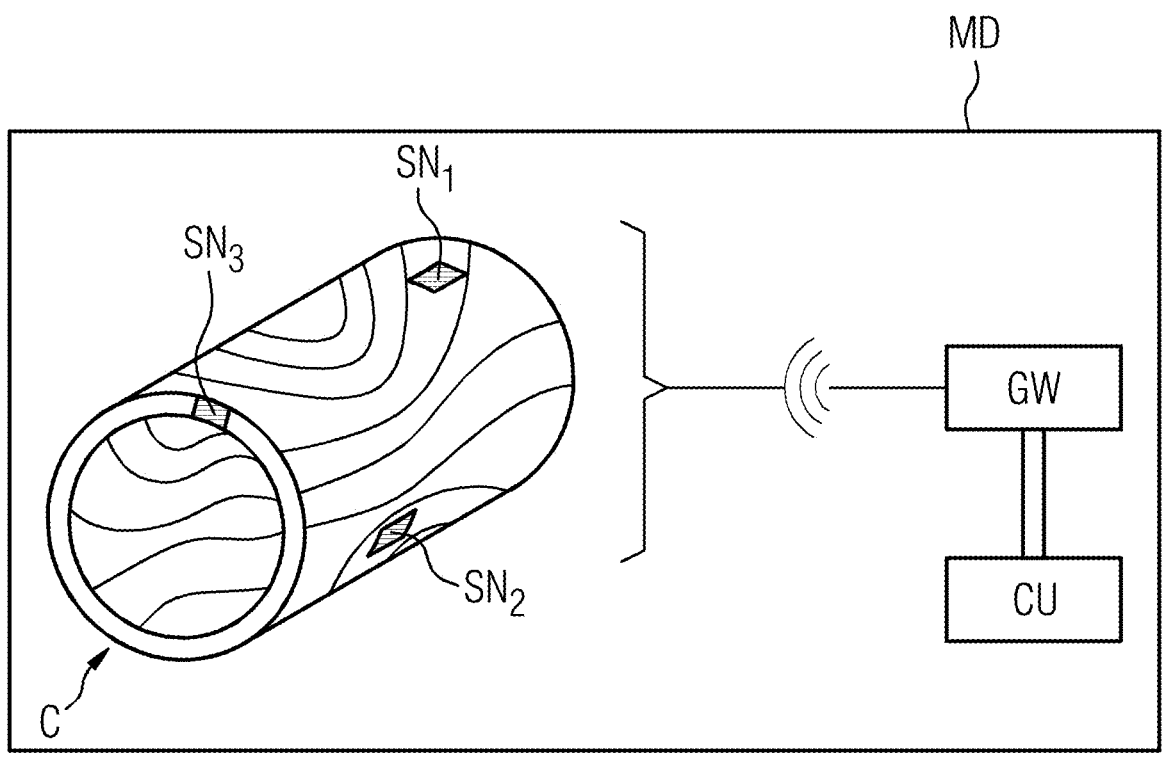
FIG. 1 is a schematic overview of a gradient coil as a component in a medical imaging apparatus according to a preferred embodiment of the invention.

As depicted in FIG. 1, a medical imaging device MD comprises several components C. In a preferred embodiment, the medical device MD is a magnetic resonance apparatus (MR apparatus) and the component is a gradient coil C. The component may also be a cryogenic cooled magnet with the MR apparatus. In another embodiment, a computed tomography apparatus is the medical device MD and an X-Ray generator as component C. The x-ray generator C may be mounted on a rotating gantry of the CT apparatus and is therefore subject to vibrations.

According to the invention, the respective embodiments of the component C are provided with sensor nodes SN, as shown in FIG. 1. The sensor nodes are electronic modules, which are integrally fitted and built-in the component C during the fabrication process of the component C. The sensor nodes SN are adapted to detect technical values, like temperature, vibrations amplitudes, mechanical stress and others. The detected measurement signals are then locally prepared on the sensor node SN for wireless transmission to a gateway GW. The gateway GW may be part of the medical device MD or may be provided as separate instance. The gateway GW is in wired connection with a control computer CU. In FIG. 1 the wired connection is represented with a double line in contrast to the wireless communication between the sensor nodes SN and the gateway GW.

This invention is based on using wireless sensors S that do not need any wired link to the medical device MD. That means the sensor nodes SN will use a wireless communication protocol (preferred radio) to talk to each other and to the medical device MD via the gateway GW. In a preferred embodiment, the sensor nodes SN build up a Wireless Sensor Network, WSN. These autonomous sensor nodes SN are spatially distributed to monitor physical or environmental conditions such as temperature, sound, pressure, etc. and to cooperatively pass their data through the network to a main or central location, in particular to the gateway GW. The wireless gateway GW within the system provides connectivity for the distributed wireless sensor nodes SN back to the wired system of the medical device or component, to be monitored (see FIG. 1).

In a further preferred embodiment, this "mesh" (set or group) of wireless sensor nodes SN use pre-certified electronic modules complete with ready-to-deploy wireless mesh networking software that communicate via a standard Internet Protocol (IP) based e.g. on the 6LoWPAN and 802.15.4e standards and enable low-power consumption and high data reliability even in harsh, dynamically changing RF environments.

The following steps or functions may be implemented and executed directly on the gateway GW or within a processing unit in the medical imaging device MD.

Preferably, the gateway GW collects and analyzes packets of sensor information flowing into a control computer CU (FIG. 1) to gain an overall understanding of the operating state of all components C in the medical imaging device MD. It changes communication control rules of the sensor nodes SN according to the actual operating state of the medical imaging device MD and other factors, like a service mode and/or a technical debugging mode. It analyzes and blocks the packets based on predefined rules. The rules mainly refer to the operation of the medical device MD and its actual processing state. For example, a rule may be "IF MR sequence=READOUT, THEN suspend transmission of detected measurement signals to gateway". It aggregates multiple sensor information, i.e. data from multiple sensor nodes SN and monitors the behavior of the entire system in an integrated manner e.g. for early detection of failures.

Furthermore, the present application has the technical advantage of combining safe control technology with security orchestration technology, consisting in network monitoring and security management that monitors real-time data flows in networks in an integrated manner. It delivers real-time security measures by changing the security remediation rules on each operating state. This is designed to enable protection against cyber-attacks that exploit control commands, which are difficult to detect and to respond to with conventional technology.

Figure 3:
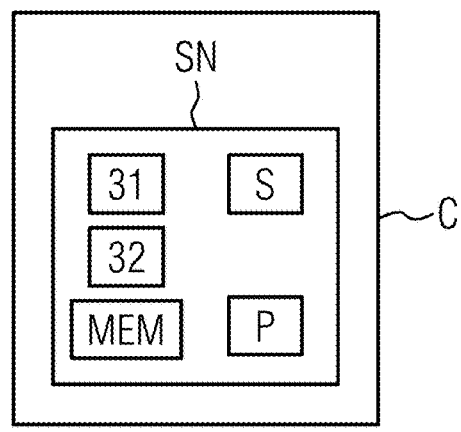
FIG. 3 is a block diagram, representing elements and electronic units of a sensor node, which is integrally built-in a component.

FIG. 3 shows the architecture of such a sensor node SN according to a preferred embodiment in more detail. The sensor node SN comprises an energy supply unit 31 for providing electricity for the sensor node SN. This makes the sensor node SN autonomous and independent of external electricity supply.

All the sensor nodes SN in the network do not require a dedicated remote power supply. Each sensor node SN uses autonomously and locally generated energy. The sensor node, therefore, comprises means to harvest energy from the operational environment. Various energy harvesting technologies can be used to power the autonomous sensor nodes SN. Energy harvesting is the process by which unused ambient energy is captured and converted into useful energy.

Energy harvesting is a way to extend the lifetime of the autonomous sensor S beyond that of known sensor nodes with a battery, because of maintenance and lifetime limitation of the battery. Thus, according to a preferred embodiment of the invention, the sensor node S is an autonomous sensor node and thus is provided without a battery. This has the technical effect that lifetime of the sensor nodes will be extended by far.

In another embodiment, the sensor nodes may still comprise a battery, which may be loaded by the energy which was generated locally in and by the sensor node S.

The dominant energy harvesting technologies are:

1. Photovoltaics—producing electricity from ambient light

2. Vibration—producing electricity from vibrations of the surface the sensor node SN, where it is deployed on (e.g. the gradient coil C). For this reason, the sensor nodes SN may comprise piezoelectric transducers, converting the mechanical energy of vibrations resulted by a combination of gravitational forces and centrifugal forces, for example occurring by rotation of the CT gantry.

3. Thermo-electrics—producing electricity from a temperature gradient

4. RF-radiation—producing electricity from a radiating field. In particular, for MR imaging, electricity is gathered from the excitation RF-energy, which is emitted by the gradient body coil C.

As a major advantage, it is possible that sensors are built-in at locations, which otherwise are difficult or even impossible to access. In a CT scanner, sensor nodes SN may be located at e.g. high voltage parts, vacuum enclosures, rotating parts of an X-ray tube. In a MR scanner, sensor nodes SN may be located at e.g. a cryocooler, a vacuum enclosure, a magnet turret, and/or superconducting coils.

As can be seen in FIG. 3, the sensor node SN additionally has at least one sensor S for signal measurement. According to the embodiment and as stated above, the sensor S may be implemented as temperature sensor, as vibration sensor and/or as mechanical stress sensor.

The sensor node SN further includes a communication unit 32. Preferably, this communication unit 32 is a wireless interface for sending and receiving data. It may comprise an antenna. Typically, the antenna is not shielded for providing high quality signal transmission. The communication unit 32 is adapted to send the detected and optionally pre-processed measurement data to the gateway GW and to receive instructions to be executed on the sensor node SN for operating the same.

The sensor node SN finally comprises a storage or a memory for locally storing the detected measurement signals. This is especially important, if the detected measurement signals need to be pre-processed locally on the sensor node SN before being transmitted to the gateway GW or if the detected measurement signals are not to be transmitted in real-time but later, for example due to activated signal detection or transmission of the medical device MD, for example within a READOUT phase during MR acquisition.

Figure 2:
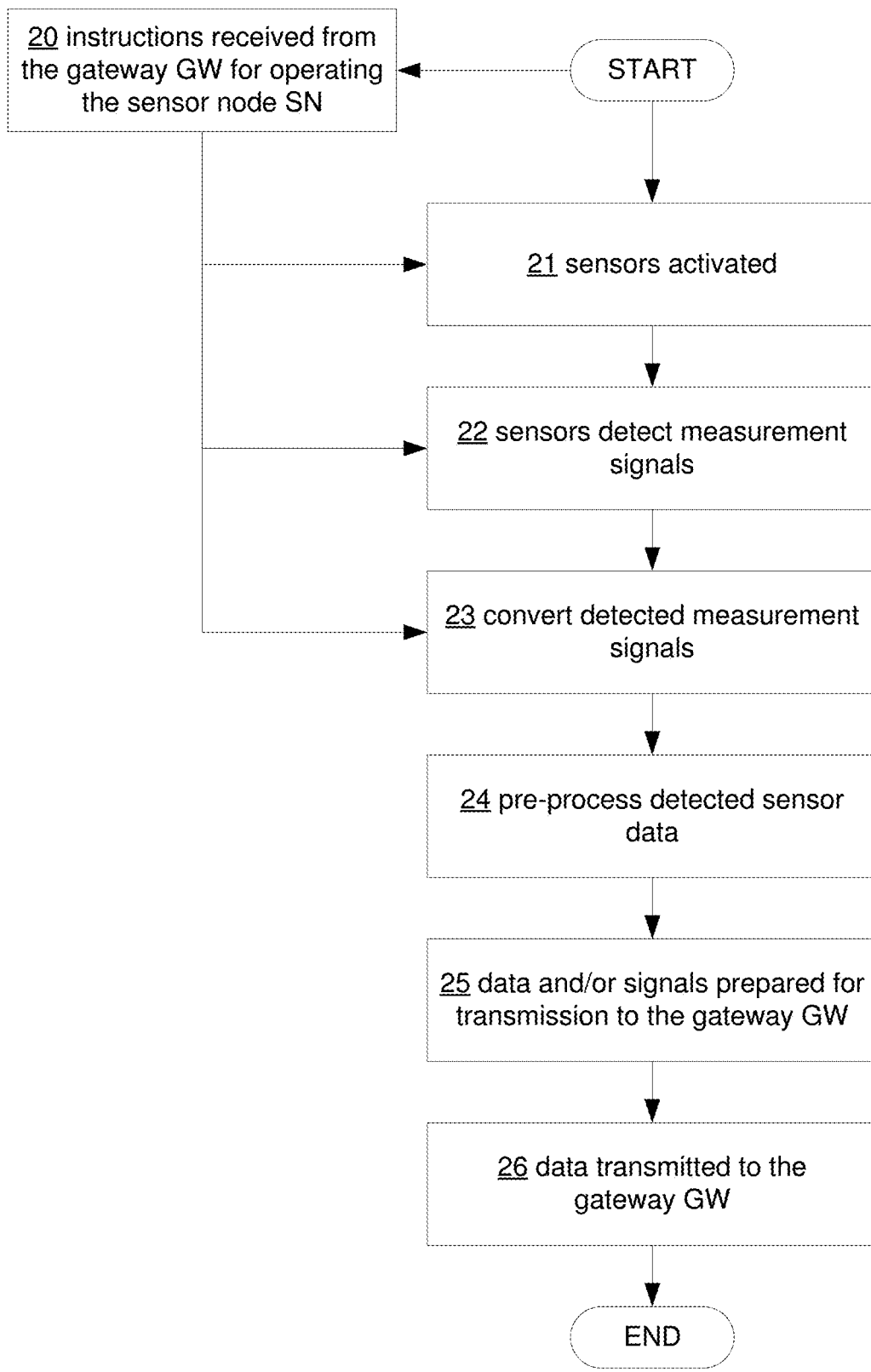
FIG. 2 is a flowchart of a method for operating a gateway for processing measurement signals from a component.

FIG. 2 is a flowchart for a method for operating a sensor node SN according to a preferred embodiment of the present invention.

After starting the method, in step 20 instructions are received from the gateway GW for operating the sensor node SN. The instructions may initiate an activation or de-activation for a signal detection of the sensor S of the sensor node SN. The instruction may for example also continue a signal detection, while interrupting or suspending transmission of the detected data to the gateway GW. According to the received instructions, the sensor node SN will be operated.

In step 21 the sensors are activated. In step 22 the sensors detect measurement signals. In step 23 the detected measurement signals are converted in a digital format (i.e. by using ADC for analog-digital conversion) and stored in the memory MEM of the sensor node SN. In step 24, the detected sensor data may optionally be pre-processed by for example conversion in another digital format. In step 25 the data and/or signals are prepared for transmission to the gateway GW. This may for example include filtering, compression and/or encryption of the data. In step 26 the data are finally transmitted to the gateway GW via a wireless interface. After that the method may end or may be executed again. All the steps, mentioned above are executed locally on the sensor node SN. The transmission in step 26 may, however, be omitted or executed at a later stage during image acquisition of the medical device MD or may even be externalized to another sending unit.

The application discloses a method for avoiding interferences produced by the RF communication between the gateway GW and the sensors S in the sensor nodes SN. Particularly relevant for a MR scanner, this interference may affect the normal operation of the medical scanner MD. During MR measurements, external RF interference generated by a "normally operating" WSN would alter the weak MR signals received from the patient body. Therefore, the invention implements a combination of means to avoid interferences, namely the following functions:

SLEEP function to avoid interference during MR measurements. After power-up reset or whenever necessary the gateway GW puts a sensor S on the respective sensor node SN in sleep mode, with all local activity reduced at a minimum. This saves energy consumption at the sensor node NS and minimizes the radiated electromagnetic interferences.

WAKEUP function, used by the gateway GW to activate a sensor S, the local signal measurement and data transmission.

MUTE function to avoid interference during MR measurements. Before starting the MR receive periods, the gateway GW broadcasts a MUTE message that will inhibit the data transmission for all or only some sensor nodes SN in the network.

UNMUTE function, after finishing the MR measurements (in particular, after the READOUT period) the gateway GW broadcasts an UNMUTE message that enable the sensor nodes SN to proceed with data transmission again.

Data logging and transmission in equivalent time with local data buffering. During the MUTE period, all the data acquired by a sensor node SN will be stored into a local memory buffer MEM, wherein each sample is supplemented with a time stamp. Later on after an UNMUTE command, the sensor node SN transmits both the newest measurements as well as the older ones until the log buffer becomes empty TIME SYNC is a broadcast message by the gateway GW used locally at sensor nodes SN to adjust the local clock, later used as timestamp for signal samples.

Figure 4:
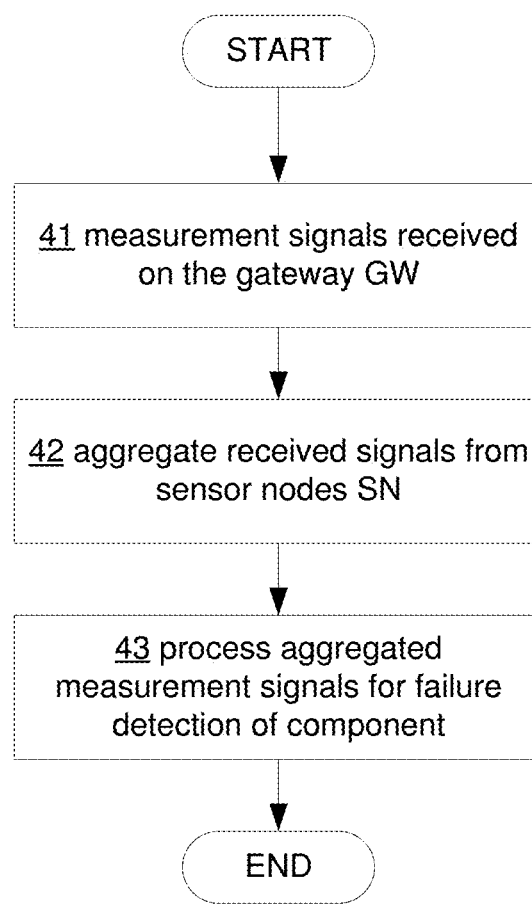
FIG. 4 is a flowchart of a method for processing measurement signals on a gateway.

FIG. 4 is a flowchart depicting method steps which are executed on the gateway GW for processing the detected measurement signals. The method usually will be executed after the method, explained above with respect to FIG. 2. After starting, in step 41 the measurement signals are received on the gateway GW. In step 42 the received signals are aggregated from all sensor nodes SN. In step 43 the received and aggregated measurement signals are processed for failure detection of the component C of the imaging device MD. After this step the method may end or may be executed iteratively or continuously.

Figure 5:
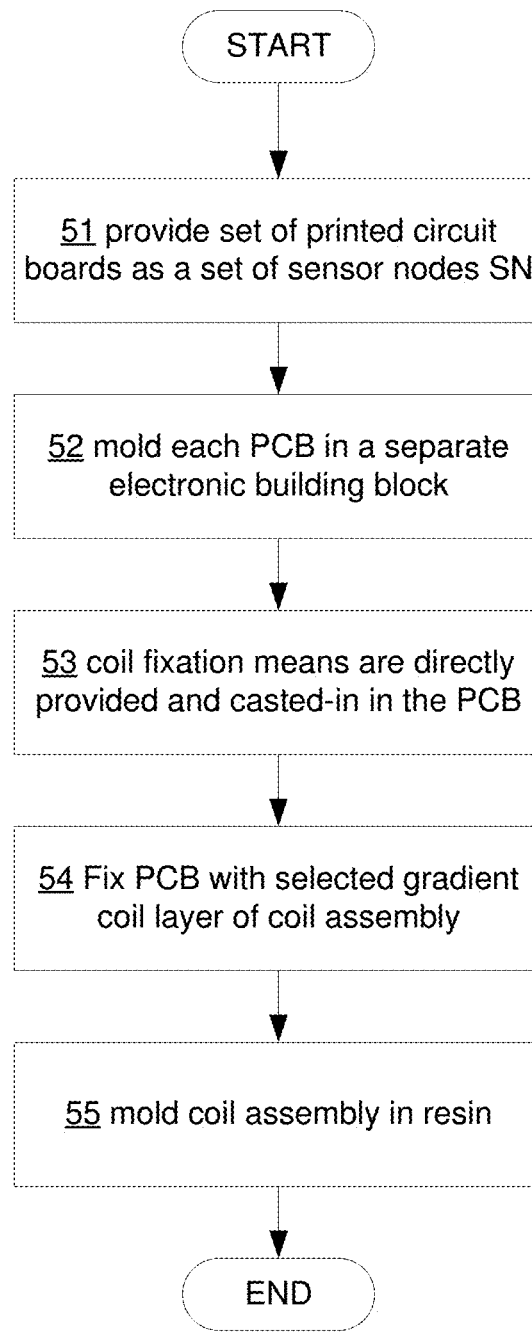
FIG. 5 is a flowchart for fabricating a gradient coil.

FIG. 5 is another flowchart showing a fabrication process of a gradient coil C according to a preferred embodiment of the present invention. In step 51 a set of printed circuit boards is provided or casted as a set of sensor nodes SN, wherein each sensor node SN is operating autonomously and produces its own electricity and transmits signals and receives instructions wirelessly. In step 52 each of the printed circuit boards (PCB) is molded in a separate electronic building block (or chunk). In step 53 coil fixation means are provided and casted-in directly in the PCB. Preferably, a thermal profile is used during casting that will not overheat the electronic circuit of the sensor nodes SN. In step 54 the electronic building block (PCB as brick/bug/element) is fixed within a selected gradient coil layer of the coil assembly. In step 55 the whole coil assembly is molded in resin.

This fabrication method is compatible with prior art fabrication methods for MR gradient coils C. The implanting of the sensor node network into the three-dimensional copper wire structure of the gradient coils C proceeds in two steps.

In a first step, the miniature sensing electronic boards are separately cast into either silicon or a resin and molded into a preferably rectangular shaped chunk with appropriate fixing structures (pots, holes, hooks) being finally cured using a modified thermal profile that will not overheat the sensitive sensor electronics, as already mentioned above.

Optionally in this step the whole electronic except the antenna could be completely shielded using a slotted copper sheet enclosure that will shield the RF fields used for MR imaging and circumvent the eddy currents produced by gradients switching.

In a second step, the resulted resin molded sensor node bricks or "bugs" will be placed and fixed within the gradient coil layers. Finally, the whole structure will be molded into resin as known from prior art. According to a preferred embodiment, a modified temperature curing profile is used, that is safe enough for the electric circuits of the sensor nodes SN.

Figure 6:
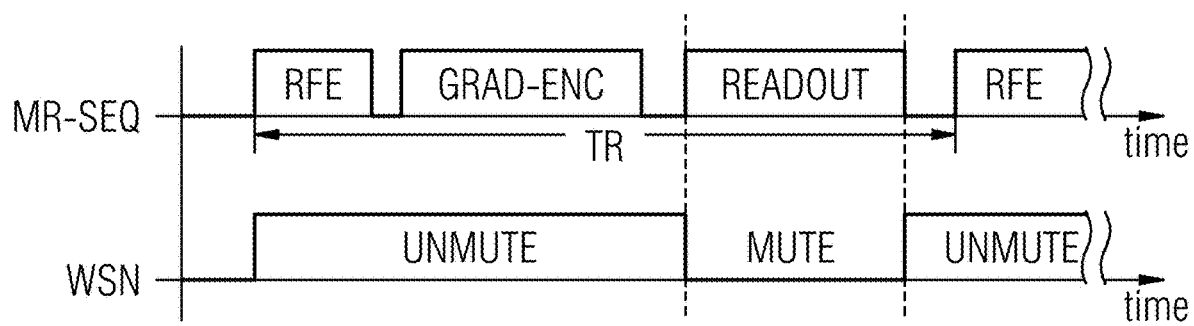
FIG. 6 schematically shows the mapping between MR sequences and transmission sequences over time.

FIG. 6 is a schematic representation of the MR sequences and their mapping to the transmission sequences of the WSN messages and related activities over time according to a preferred embodiment of the invention. Using the gradient coils, a selection gradient may be applied to select, for example a thin slice in the examination space of the patient. Subsequently, the transmitter coil may emit a high power radio frequency/RF electromagnetic excitation pulse REF, whereby the spins in the selected slice in the body of the patient are excited. The excited spins relax to their equilibrium states and emit RF magnetic resonance signals which are received by a receiver or scanner coil. The RF magnetic resonance signals are, for example generated as gradient echo signals or as spin echo signals. From these magnetic resonance signals an image signal may be reconstructed.

Turning now again to FIG. 6, in the first line above, a MR sequence is depicted. In this example, it consists of the RF excitation phase REF, followed by a gradient encoding phase GRAD-ENC, followed by a READOUT phase. This sequence is executed repeatedly (repetition time TR). During the GRAD-ENC phase the scanner activates the gradient coil to generate signal encoding and in the READOUT phase, which represents the measurement time window, the scanner receives the RF signals out of the patient body.

In the second line below in FIG. 6, an UNMUTE phase is followed by a MUTE phase. It can be seen, that during READOUT of the MR device, the sensor system is in the MUTE mode, whereas during other MR phases (REF, GRAD-ENC) the sensor system is operated in an UNMUTE mode. During UNMUTE mode and in particular during the RFE phase, the sensor node SN harvests parts of this RF energy, which may be used to reload the internal battery and during the GRAD-ENC phase, the sensor node SN harvests vibrational energy which for example may be used to reload the local sensor node battery. As can be seen in FIG. 6, during READOUT phase, the sensor node SN is in MUTE mode and may log data but does not transmit signals for not impairing image quality.

While the current invention has been described in relation to its preferred embodiments, it should be understood that this description is for illustrative purposes only. For example, the imaging device MD may be an MR or a CT apparatus.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for detecting measurement signals during a medical imaging procedure executed by a medical imaging apparatus, said method comprising:
   detecting respective measurement signals with a plurality of sensor nodes that are integrated in said medical imaging apparatus, by operating each sensor node autonomously and wirelessly; and
   operating a gateway circuit to locally prepare the plurality of detected signals for transmission from said gateway circuit according to an interference-free instruction protocol that includes a set of instructions issued by the gateway circuit, for reception and processing at said sensor nodes, the set of instructions including a MUTE and UNMUTE instruction and a SLEEP and WAKE-UP instruction, wherein:
   the MUTE instruction serves to initiate a MUTE mode in which the sensor nodes are configured to disable data transmission while continuing and to detect the measurement signals and store corresponding data, the MUTE mode being activated during a readout of the medical imaging apparatus operating as a magnetic resonance imaging apparatus;
   the UNMUTE instruction serving to initiate an UNMUTE mode in which the sensor nodes are configured to harvest ambient energy from the medical imaging apparatus, which is activated during a radio frequency excitation (RFE) phase and gradient encoding (GRAD-ENC) phase of the medical imaging device operating as the magnetic resonance imaging device;
   the SLEEP instruction serves to initiate a SLEEP mode in which the sensor nodes are configured to disable data transmission and disable detection of the measurement signals; and
   the WAKE-UP instruction serves to initiate a WAKE-UP mode in which the sensor nodes are configured to enable the detection of the measurement signals and enable data transmission.

2. A method as claimed in claim 1 comprising measuring a respective local value individually with each sensor of a sensor node, selected from the group consisting of a temperature value, a vibration amplitude, a mechanical stress value, a pressure value an acceleration value, a voltage value, a current value, a flow value, an electric field value, and a magnetic field value.

3. A method as claimed in claim 1 comprising, when locally preparing said plurality of detected signals, storing or pre-processing the detected measurement signals.

4. A method as claimed in claim 1 comprising locally preparing the plurality of detected signals for transmission from said gateway circuit according to said interference-free instruction protocol so as to avoid interference to the detected measurement signals, when transmitted according to said protocol, by signals produced by said medical imaging apparatus as part of said medical imaging procedure.

5. A method as claimed in claim 1 wherein said set of instructions further comprises:
   a TIME SYNC instruction which serves to adjust a respective local clock on the sensor nodes with a gateway clock.

6. A method as claimed in claim 1 comprising implementing an automatic data-loss-prevention procedure that initiates energy-provision functions for further operating each sensor node under low energy conditions.

7. A method as claimed in claim 6 wherein said data-loss-prevention procedure comprises sending an SOS message from a respective sensor node to said gateway circuit, if a local energy reserve at the respective sensor node decreases below a predetermined threshold.

8. A method as claimed in claim 6 comprising initiating said energy-provision function by said gateway circuit in reply to receiving said SOS message from a respective sensor node, with said gateway circuit then sending an instruction to the medical imaging apparatus to activate a source of energy of the medical imaging apparatus in order to provide energy to the sensor node that sent the SOS message.

9. A method as claimed in claim 1 wherein the sensor nodes are configured to harvest radio frequency (RF) energy during the RFE phase and vibrational energy during the GRAD-ENC phase.

10. A component for a medical imaging apparatus, said component comprising:
a component body designed to perform a function in a medical imaging procedure executed by the medical imaging apparatus; and
a set of wirelessly and autonomously operating sensor nodes integrated in, and fabricated in one piece with, said component body, each sensor node including an energy supply unit that provides electricity that operates the sensor node, at least one sensor element that detects at least one type of measurement signal, and a communication unit, and a memory that locally stores the measurement signals detected by said at least one sensor of said sensor node, wherein the sensor nodes are configured to operate in:
a MUTE mode in which the sensor nodes are configured to disable data transmission while continuing and to detect the measurement signals and store corresponding data, the MUTE mode being activated during a readout of the medical imaging apparatus operating as a magnetic resonance imaging apparatus;
an UNMUTE mode in which the sensor nodes are configured to harvest ambient energy from the medical imaging apparatus, which is activated during a radio frequency excitation (RFE) phase and gradient encoding (GRAD-ENC) phase of the medical imaging device operating as the magnetic resonance imaging device;
a SLEEP mode in which the sensor nodes are configured to disable data transmission and disable detection of the measurement signals; and
a WAKE-UP mode in which the sensor nodes are configured to enable the detection of the measurement signals and enable data transmission.

11. A component as claimed in claim 10 wherein each sensor node comprises a copper sheet enclosure that at least partly shields the sensor node from signal interferences with signals produced by said medical imaging apparatus during said medical imaging procedure.

12. A component as claimed in claim 10 wherein at least one of said sensor nodes comprises a processor that pre-processes the detected measurement signals thereof for transmission.

13. A component as claimed in claim 10 wherein said medical imaging apparatus is magnetic resonance scanner, and wherein said component body is a gradient coil.

14. A component as claimed in claim 10 wherein said medical imaging apparatus is a magnetic resonance scanner, and wherein said component body is a cryogenically-cooled superconducting magnet.

15. A component as claimed in claim 10 wherein the sensor nodes are configured to harvest radio frequency (RF) energy during the RFE phase and vibrational energy during the GRAD-ENC phase.

16. A medical imaging system comprising:
a medical imaging device that executes a medical imaging procedure;
a component designed to perform a function in said medical imaging procedure executed by said medical imaging device; and
a set of wirelessly and autonomously operating sensor nodes integrated in, and fabricated in one piece with, said component, each sensor node including an energy supply unit that provides electricity that operates the sensor node, at least one sensor element that detects at least one type of measurement signal, and a communication unit, and a memory that locally stores the measurement signals detected by said at least one sensor of said sensor node, wherein the sensor nodes are configured to operate in:
a MUTE mode in which the sensor nodes are configured to disable data transmission while continuing and to detect the measurement signals and store corresponding data, the MUTE mode being activated during a readout of the medical imaging apparatus operating as a magnetic resonance imaging apparatus;
an UNMUTE mode in which the sensor nodes are configured to harvest ambient energy from the medical imaging apparatus, which is activated during a radio frequency excitation (RFE) phase and gradient encoding (GRAD-ENC) phase of the medical imaging device operating as the magnetic resonance imaging device;
a SLEEP mode in which the sensor nodes are configured to disable data transmission and disable detection of the measurement signals; and
a WAKE-UP mode in which the sensor nodes are configured to enable the detection of the measurement signals and enable data transmission.

17. A medical imaging system as claimed in claim 16 wherein the sensor nodes are configured to harvest radio frequency (RF) energy during the RFE phase and vibrational energy during the GRAD-ENC phase.

* * * * *